(12) United States Patent
Christensen et al.

(10) Patent No.: US 11,869,636 B2
(45) Date of Patent: Jan. 9, 2024

(54) ANALYSIS INSTRUMENT (71) Applicant: Foss Analytical A/S, Hilleroed (DK)

(72) Inventors: Rasmus Lundgaard Christensen, Hilleroed (DK); Tamir Gil, Hilleroed (DK); Rasmus Vistisen, Hilleroed (DK); Malin Damm, Hilleroed (DK)

(73) Assignee: FOSS Analytical A/S, Hilleroed (DK)

( * ) Notice: Subject to any disclaimer, the term of this patent is extended or adjusted under 35 U.S.C. 154(b) by 414 days.

(21) Appl. No.: 17/052,059

(22) PCT Filed: May 20, 2019

(86) PCT No.: PCT/IB2019/054146
§ 371 (c)(1),
(2) Date: Oct. 30, 2020

(87) PCT Pub. No.: WO2020/030987
PCT Pub. Date: Feb. 13, 2020

(65) Prior Publication Data
US 2021/0241868 A1 Aug. 5, 2021

(30) Foreign Application Priority Data

Aug. 9, 2018 (DK) .............................. PA201800449

(51) Int. Cl.
*G16H 10/40* (2018.01)
*G01N 35/00* (2006.01)

(52) U.S. Cl.
CPC ....... *G16H 10/40* (2018.01); *G01N 35/00732* (2013.01); *G01N 2035/00831* (2013.01); *G01N 2035/00891* (2013.01)

(58) Field of Classification Search
CPC ... G01N 35/00732; G01N 2035/00831; G01N 2035/00891; G16H 10/40
See application file for complete search history.

(56) References Cited

U.S. PATENT DOCUMENTS

| 5,218,971 A | 6/1993 | Minami et al. |
| 5,777,902 A | 7/1998 | Ono et al. |

(Continued)

FOREIGN PATENT DOCUMENTS

| DE | 102014204882 A1 | 9/2014 |
| TW | 200704928 A | 2/2007 |
| WO | WO-2015051906 A1 | 4/2015 |

OTHER PUBLICATIONS

Danish Search Report for Danish patent application No. PA201800449 dated Feb. 11, 2019.

(Continued)

*Primary Examiner* — Shogo Sasaki
(74) *Attorney, Agent, or Firm* — Harness, Dickey & Pierce, P.L.C.

(57) ABSTRACT

An analysis instrument comprises a sample receiving section for receiving samples provided by a plurality of users, an analysis section operable to receive an aliquot of each received sample, perform an analysis of each received aliquot, and generate an output based on the analysis, and a presentation section adapted to present the output in a human discernable format. The analysis instrument further includes an identification section adapted to autonomously generate an identifier unique to each user and each sample provided thereby and to supply each identifier for presentation by the presentation section in a human discernable format together with a portion of the output that corresponds with one or more samples provided by a user to which the identifier is unique. Each identifier consists of one or more graphic symbols, one or more colours, and/or one or more numbers.

20 Claims, 4 Drawing Sheets

(56) References Cited

U.S. PATENT DOCUMENTS

| | | | |
|---|---|---|---|
| 8,343,423 B2* | 1/2013 | Mori | G01N 35/00663 |
| | | | 422/65 |
| 10,146,909 B2* | 12/2018 | Dimov | G16H 20/10 |
| 2003/0073124 A1 | 4/2003 | Bowman et al. | |
| 2010/0111765 A1 | 5/2010 | Gomm et al. | |
| 2010/0222939 A1 | 9/2010 | Namburu et al. | |
| 2010/0332191 A1 | 12/2010 | Hamada et al. | |

OTHER PUBLICATIONS

International Search Report PCT/ISA/210 for International Application No. PCT/IB2019/054146 dated Nov. 8, 2019.
Written Opinion of the International Searching Authority PCT/ISA/237 for International Application No. PCT/IB2019/054146 dated Nov. 8, 2019.

* cited by examiner

ANALYSIS INSTRUMENT

CROSS-REFERENCE TO RELATED APPLICATIONS

This application is a National Stage of PCT/IB2019/054146, filed on May 20, 2019, which claims priority to Danish Patent Application PA201800449, filed on Aug. 9, 2018 in the Danish Patent and Trademark Office, the entire contents of each of which are incorporated herein in their entirety.

BACKGROUND

The present invention relates to an analysis instrument and in particular to an analysis instrument for use in a multi-user environment.

An analysis instrument generically comprises a sample receiving section configured to receive a number of samples for analysis; an analysis section having an analysis modality configured to receive an aliquot of each of the number of received samples, to perform an analysis of each of the received aliquots and to generate an output representative of results of the performed analysis; and a presentation section configured to receive the output from the analysis section and to present the output in a human discernable format.

When such an analysis instrument is deployed in a multi-user environment in which a plurality of users each bring their own samples for analysis it may become difficult to correlate the results of the performed analysis with the particular user providing the samples from which the results originate and also with different samples provided by the same user. In such a multi-user and/or multi-sample environment the access to the analysis instrument is often restricted to only one user at a time, even, under some circumstances also to only one sample at a time. That is to say, a subsequent user cannot introduce samples for analysis or the same user may not be able introduce new samples until the results of the analysis of the samples introduced by the preceding user and/or preceding sample are presented by the presentation section.

This may lead to underutilization of the analysis instrument, particularly where the sample receiving section is able to receive a plurality of samples at any one time but a user provides less than this plurality for analysis. User congestion may also be a problem as each user must wait in turn to use the analysis instrument, this may be exacerbated in cases where a sample received into the instrument must undergo some form of chemical reaction before analysis can be performed.

SUMMARY

According to a first aspect of the present invention there is provided an analysis instrument comprising a sample receiving section configured to receive a number of samples provided by each of a number of users; an analysis section having an analysis modality adapted to receive an aliquot of each of the number of received samples, to perform an analysis of each of the received aliquots and to generate an output dependent on the performed analysis; and a presentation section adapted to receive the output from the analysis section and to present the output in a human discernable format; characterised in that the analysis instrument further comprises an identification section adapted to generate an identifier unique to each one of the number of users and to supply the identifier for use in the presentation section; and in that the presentation section is further adapted to present the identifier in a human discernable format together with a portion of the output corresponding with the samples provided by a user to which the identifier is unique. In this manner the results of analysis performed on samples from an individual user can be uniquely identified to any interested party, including to the user, as originating from a particular user.

The identification section is specifically adapted to autonomously generate a sample identifier unique to each sample presented by a user at the sample receiving section as a part of the identifier. This has an advantage that results from different samples may be readily identified by the user who provided those samples without user input. Usefully the sample identifier may be a colour and in some embodiments a light source may be provided to illuminate the sample receiving section, preferably also the sample in respect of which the sample identifier is generated, with that colour.

In some embodiments the identification section of the analysis instrument according to the present invention is adapted to generate the identifier consisting of one or more of (i) one or more graphic symbols, such as letters of an alphabet or geometric shapes; (ii) one or more colours and (iii) one or more numbers. This has an advantage that an identifier, such as an alpha-numeric; a coloured shape; or a combination of these two, may be generated without external input.

In some embodiments the identification section comprises a reader adapted to read identification information originating from the user and to employ the identification information in the generation of the identifier. This information may be biometric information. Thus, it may be possible for the identifier to contain specific information chosen by the user or other party. Usefully the biometric information may be a still or a moving image captured by a camera which forms a part of the reader. This has an advantage that the biometric information may be acquired with a minimum of input by the user. Additionally or alternatively, the biometric information may be voice information recorded by a microphone which forms part of the reader. This information may be stored on a carrier, such as a barcode, QR code or an RFID chip located with the user, and the reader comprises a complementary unit, such as an optical reader or wireless receiver, for remotely accessing this information when a user is in the proximity of the analysis instrument. Information may then be transferred from the user to the instrument without interaction of the user.

In some embodiments the presentation section is adapted to also present the identifier in human discernable format separate from and before presenting it together with, the portion of the output. In this manner the user or other interested party may be made aware of the identifier being employed to identify a particular user before the results of any analysis is presented.

In some embodiments the presentation section is adapted to receive the output from the analysis section via a telecommunication device. This facilitates the remote presentation of information generated in the instrument to a user or other party, such as a facility operator, having a need to know the origin of the samples and the results of its analysis.

It will be appreciated that some or all of the features of some or all of the embodiments may be combined to provide other embodiments which still fall within the scope of the invention as claimed and which will retain the advantages associated with those features that are so combined.

According to a second aspect of the present invention there is provided a method of operating an analysis instrument according to the first aspect of the present invention comprising the steps of: receiving at a sample receiving section a number of samples provided by each of a number of users; performing at an analysis section an analysis of sample aliquots obtained from each of the number of samples received at the sample receiving section; generating an output dependent on the performed analysis; presenting at a presentation section the generated output in a human discernable format; wherein the method also comprises the steps of: autonomously generating at an identification section an identifier unique to each one of the number of samples, the identifier consisting of one or more of (i) one or more graphic symbols, such as letters of an alphabet or geometric shapes; (ii) one or more colours and (iii) one or more numbers; and suppling the identifier for presentation at the presentation section together with a portion of the generated output corresponding with the samples provided by a user to which the identifier is unique.

BRIEF DESCRIPTION OF THE DRAWINGS

In order to provide a better understanding of the present invention, as well as of these and other advantages, non-limiting exemplary embodiments will be described with reference to the drawings of the accompanying figures, of which.

DETAILED DESCRIPTION

Figure 1:
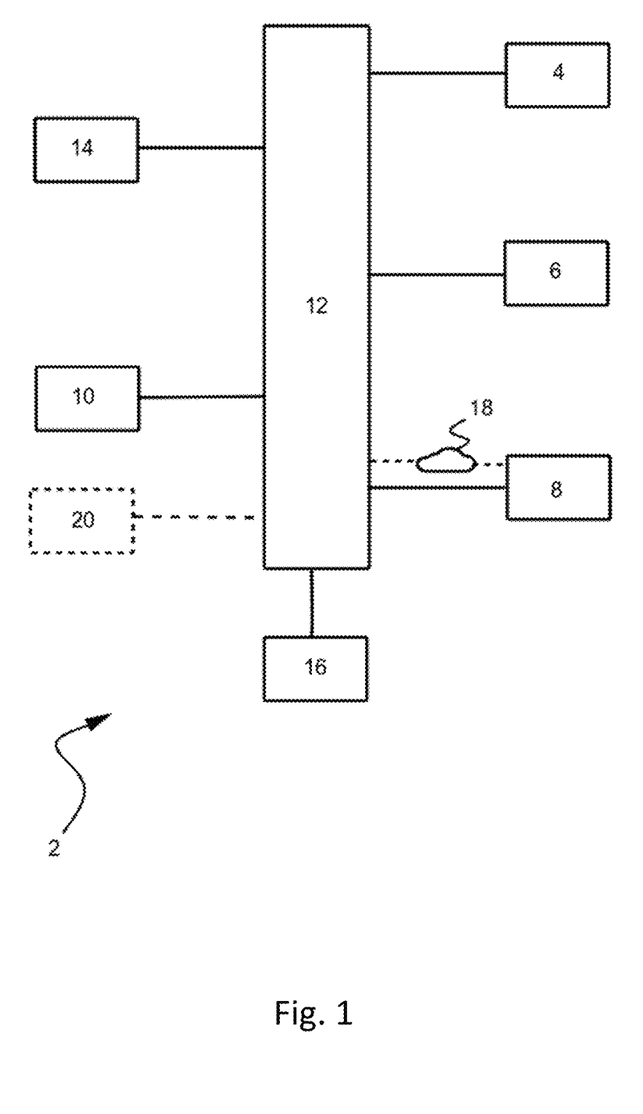
FIG. 1 shows a functional block diagram of an analysis instrument according to the present invention.

With reference to the functional block diagram of FIG. 1, an analysis instrument 2 is shown as comprising a sample receiving section 4; an analysis section 6; a presentation section 8 and an identification section 10 which, in the present embodiment, are all operably connected to and controlled by a common control unit 12. The control unit 12 may comprise a suitably programmed microprocessor adapted to execute program code to control the operation of the analysis instrument 2 and to process data generated thereby. In other embodiments some or all of the functionality of the control unit 12 may be provided by several physically separate elements configured to function as the single control unit 12, which elements may form parts of the other functional elements of the analysis instrument 2. In the present embodiment, optionally a user input section 14 and a memory storage unit 16 are also provided, here in operable connection to the control unit 12, and may also form a part of the control unit 12.

The sample receiving section 4 is adapted to receive a number of samples and may, for example, comprise a carousel for holding a plurality of sample containers; or a transport band on which a plurality of sample containers may be located or a station for receiving single sample containers. The sample receiving section 4 is adapted to operate, here under the control of control unit 12, to take an aliquot, including the entire so provided sample, of each so provided sample for subsequent analysis. The sample receiving section 4 may, in some embodiments, also be provided with a buffer section where a plurality of the sample aliquots may be held, for example to facilitate incubation or chemical reaction, until transfer of some or all of the held sample aliquots to the analysis section 6 for analysis.

The analysis section 6 is adapted to receive the sample aliquots transferred from the sample receiving section 4. The analysis section 6 operates, in the present embodiment under control of control unit 12, to perform an analysis of these samples, for example in respect of one or both of their compositional and physical properties, and to generate an output, typically a digital output, representative of the results of the performed analysis for input to the control unit 12 or other data processing device. The analysis metrology employed in the analysis section 6 may be any known suitable metrology, for example optical spectroscopy such as Fourier transform interferometry or absorption/transmission spectroscopy, flow cytometry or wet chemical analysis such as enzyme-linked immunosorbent assay (ELISA) tests. The signals generated by this analysis metrology may then be passed to the control unit 12 or other suitably programmed data processor where they are processed in a known manner in order to determine compositional and/or physical properties of the analysed sample for use in generating information for presentation by the presentation section 8.

The presentation section 8 is adapted to present information in a human discernible format and in the present embodiment is operated under the control of control unit 12. Information to be present includes information which is dependent on the output from the analysis section 6 to which has been added, here in the control unit 12, a unique identifier autonomously generated by the identification section 10. The information may, for example, be presented as a graphical display on one or more monitors, which monitors are then components of the presentation section 8. The presentation section 8 may be adapted to present information at a plurality of different locations, in which case, the information presented may be the same or may be different at some or all of the plurality of different locations but still be dependent on the output of the analysis section 6 and still include the unique identifier. For example, at one location a third party, such as say a plant manager, may receive via a telecommunications system 18 such as via the internet compositional and/or physical properties of the sample resulting from the performance of the analysis by the analysis section 6, whereas a truck driver (user) may receive a direction as how to proceed with the cargo from which the sample or samples being analysed were taken. This direction may be generated in the control unit 12 which may be programmed to compare the compositional and/or physical properties of the sample resulting from the performance of the analysis with preset values and to generate the direction in dependence thereof, for example the performance of the analysis by the analysis section 6 may indicate the presence of a contaminant in the sample in which case the direction generated in the control unit 12 may be a refusal of the cargo.

The identification section 10 may comprise a suitably programmed microcomputer configured to autonomously generate an identifier that is unique to each sample provided by a current user of the analysis instrument 2 and may be formed integral with the control unit 12. The identification section 10 may, for example, be operated under the control of control unit 12 to execute programming code which when executed causes the identification section 10 to generate a random alpha-numeric symbol as the identifier.

Irrespective of the form of the user identifier that is generated by the identification section 10, the so generated identifier is stored, such as in memory storage unit 16 for later association, in the present embodiment in the control unit 12, with the results of the analysis performed by the analysis section 6 on sample aliquots provided by the user in respect of which the user identifier is generated. In some embodiments the unique identifier is passed to the presentation section 8 which is controlled by the control unit 12 to present the unique identifier to the user independently of and before the presentation of the information dependent on the output from the analysis section 6, possibly together with an associated user identifier.

The user input section 14 may comprise a touch screen or an alpha numeric keypad via which a user may input information related to the sample, such as its origin and/or transport related storage conditions. In some embodiments the user input section 14 may be employed to input user contact details such as a mobile telephone number which may be used by the presentation section 8 to provide information to the user. The user input information is then stored in the memory storage unit 16 for later association with the results of the analysis performed by the analysis section 6 by means of the control unit 12. In some embodiments the user input section 14 may be employed to register certain responses of the user to requests for information from the analysis instrument 2.

In some embodiments a reader 20 may be provided in addition to or instead of the user input section 14 in order to facilitate the input of previously generated information. The reader 20 may be configured to read a label, such as a bar code a QR-code or an Radio Frequency (RF) tag, located with the user or affixed to the sample container(s)—in which latter case the reader 20 may conveniently be integral with the sample receiving section 4—and containing the previously generated information.

In some embodiments the sample receiving section 4 may comprise a sample depot and a separate sample uptake which is located remote of the sample depot and local of the analysis section 6. A user deposits samples at the sample depot from where they are transported to the sample uptake which is operated to extract a sample aliquot for subsequent analysis in the analysis section 6. In these embodiments the reader 20 may advantageously comprise two reader units disposed to read the same label affixed to the sample container(s), a first reader unit located at the sample depot and a second reader unit located at the sample uptake and the presentation section 8 may comprise means to present the user identifier in a human discernible format to the user in the vicinity of the sample depot.

By way of example only, a particular embodiment of an analysis instrument according to the present invention will now be described in greater detail in order to further highlight the advantages of the present invention. This description is made with reference to FIG. 2, in which a milk analysis instrument 22 is represented schematically with the functional sections equivalent to those of FIG. 1 illustrated by broken line constructions and referenced using the same reference numerals as used with respect to that FIG. 1.

Figure 2:
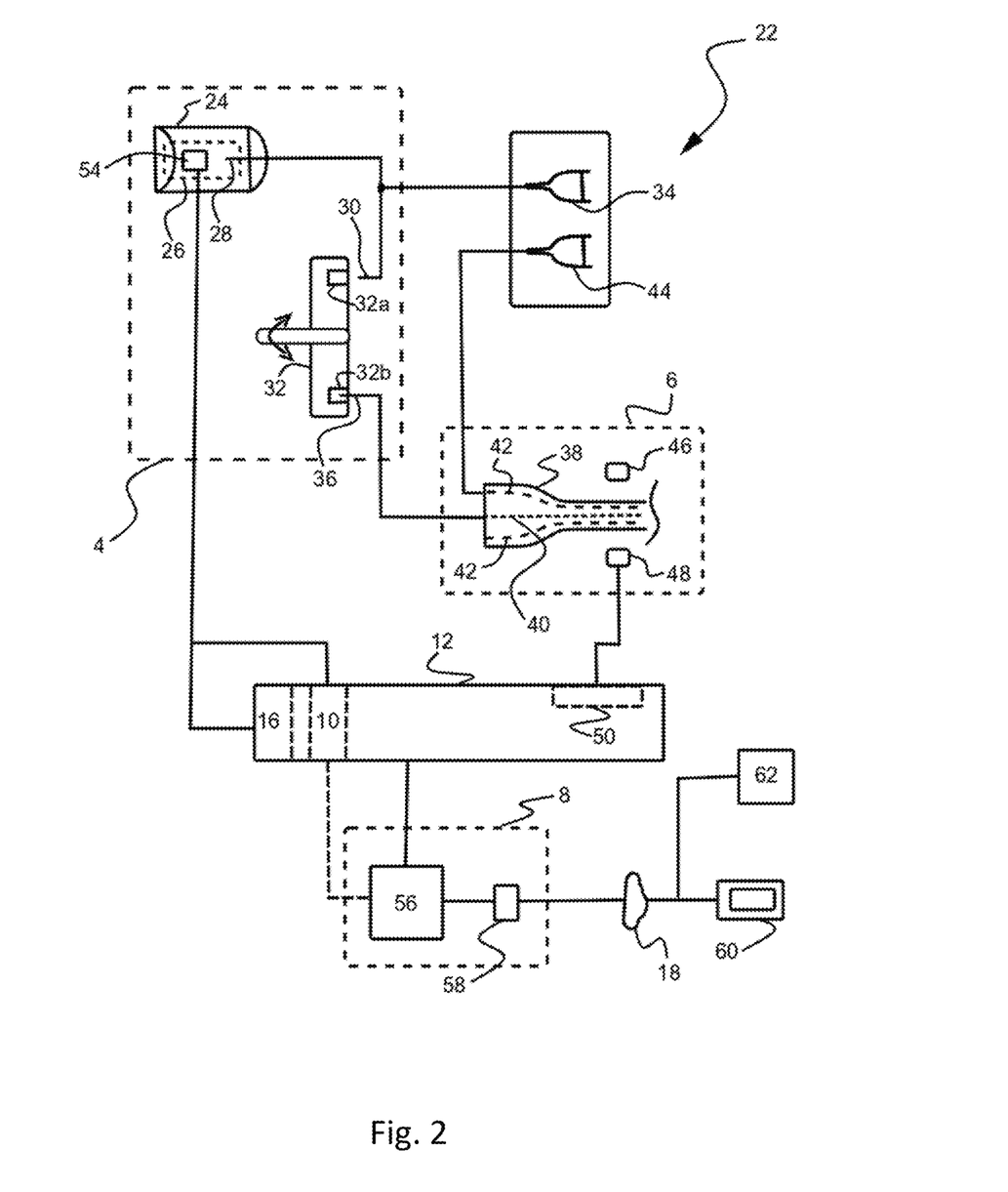
FIG. 2 shows a schematic diagram of a milk analysis instrument according to the present invention.

The milk analysis instrument 22 has a sample receiving section 4, here comprising a pipetting station 24 which is configured to receive a single sample container 26 (not part of the milk analysis instrument 22); a first pipette 28 which is moveable for lowering into and removal out of a milk sample in the sample container 26 and is configured to extract a sample aliquot from the milk sample; a second pipette 30 in liquid connection with the first pipette 28 and is configured to deposit the sample aliquot into a buffer, in this embodiment a rotatable incubation unit 32, for queuing samples for analysis. The rotatable incubation unit 32, in the present embodiment, has a plurality of wells (here only two illustrated 32a, 32b) located about its periphery. The incubation unit 32 is operable to rotate a vacant well (here 32a) to a position in which it can receive milk from the second pipette 30 which has been extracted from the sample container 26 by first pipette 28.

Reagent for the extraction of components of interest in the milk may be provided, for example as a dry reagent in vacant well (32a) or from a separate liquid reagent source 34 via the second pipette 30, to react with the milk sample in the well 32a. Typically some time (incubation period) is required for the reagent to properly react with the sample and extract the components of interest. During the incubation period for a sample in one well (32b say) the incubation unit 32 may be caused to rotate so as to present several more vacant wells (32a) to the second pipette 30 for receiving other milk samples. At completion of the incubation period for a sample in one well 32b the control unit 12 operates to cause the incubation unit 32 to rotate so as to bring that well 32b under a third pipette 36 which is then operated to extract a liquid sample from that well 32b. In some embodiments the second 30 and the third 36 pipettes may be replaced by a single moveable pipette and additionally the incubation unit 32 may be stationary.

It will be appreciated from the description below that without the generation of a unique (i.e. unique to each sample and each user of the instrument currently having samples under analysis) user identifier (hereinafter also referred to as "user ID") which is linked to the sample in the milk analysis instrument 22 the introduction of a new sample by a new user would need to be delayed until at least after the incubation period for a sample already received in to the milk analysis instrument 22 is completed.

An analysis section 6 here comprises a conventional flow cytometer 38 for analysis of the liquid sample extracted by the third pipette 36 from the well 32b containing a reacted milk sample. As is known, the extracted liquid sample is injected into the flow cytometer 38 as a flow stream 40 surrounded by a flowing sheath liquid 42 which is here supplied from a sheath liquid supply 44. As is known, a laser source 46 and complementary detector 48 are provided as components of the flow cytometer 38 and the detector 48 is configured with its output in operable connection to a signal analyser 50 which here is formed as a part of a control unit 12 and is configured to analyse the output of the detector 48 to generate information related to the detected presence or absence of components of interest in the milk sample from which the sample aliquot was originally removed. This information may for example be a measure of the amount of the component of interest in the milk or may be an indication that the component of interest is present.

An identification section 10 is here realised as a part of the control unit 12 and is configured to generate a user ID which is unique to each sample provided by a current user of the milk analysis instrument 22. The identification section 10 is configured to generate this user ID in response to a signal identifying the presence of a new sample for intake into the milk analysis instrument 22. This signal is, in the present embodiment, generated automatically upon the placement of a sample container 26 in the pipetting station 24 of the sample receiving section 4. A reader 54, here a conventional barcode reader, is operable under control of control unit 12 to read a barcode located on the sample container 26 when located in the pipetting station and to generate a signal dependent on the information contained in the barcode and on the detection of the presence of the barcode itself. The latter is used by the identification section 10 to initiate the generation of a user ID. A memory storage unit 16, is connected to receive the user ID generated by the identification section and hold it for association with the information related to the presence or the absence of a component of interest in the milk which is generated by the signal analyser 50. The user ID is also passed for presentation to the relevant user such as for display on one or more screens 56 which form a part of a presentation section 8 of the milk analysis instrument 22.

One screen 56 is, in the present embodiment, located proximal the pipetting station 24 so as to be viewable by a user who has located a sample container 26 in the pipetting station 24 and the identification section 10 is configured to pass the user ID to the presentation section 8 for display on this screen 56 independently of and before the analysis of the milk sample.

The presentation section 8 of the present embodiment also comprises a transmitter device 58, such as a modem, for communication with a remote receiver, such as a mobile telephone 60 located with the user and/or a modem 62 or remote screen (not shown) located remote of the milk analysis instrument 22, such as at a control location of a milk receival site, or at a data storage/processing facility, or at a location at which the user is expected to be.

While the invention has been described and illustrated with reference to a milk analysis instrument it will be understood that the advantages of the invention may be obtained with other types of analysis instrument, with other configurations of functional elements and equivalents thereof and with or without some or all functional elements being located in a same housing so that the invention is limited only by the scope of the claims appended hereto.

Figure 3:
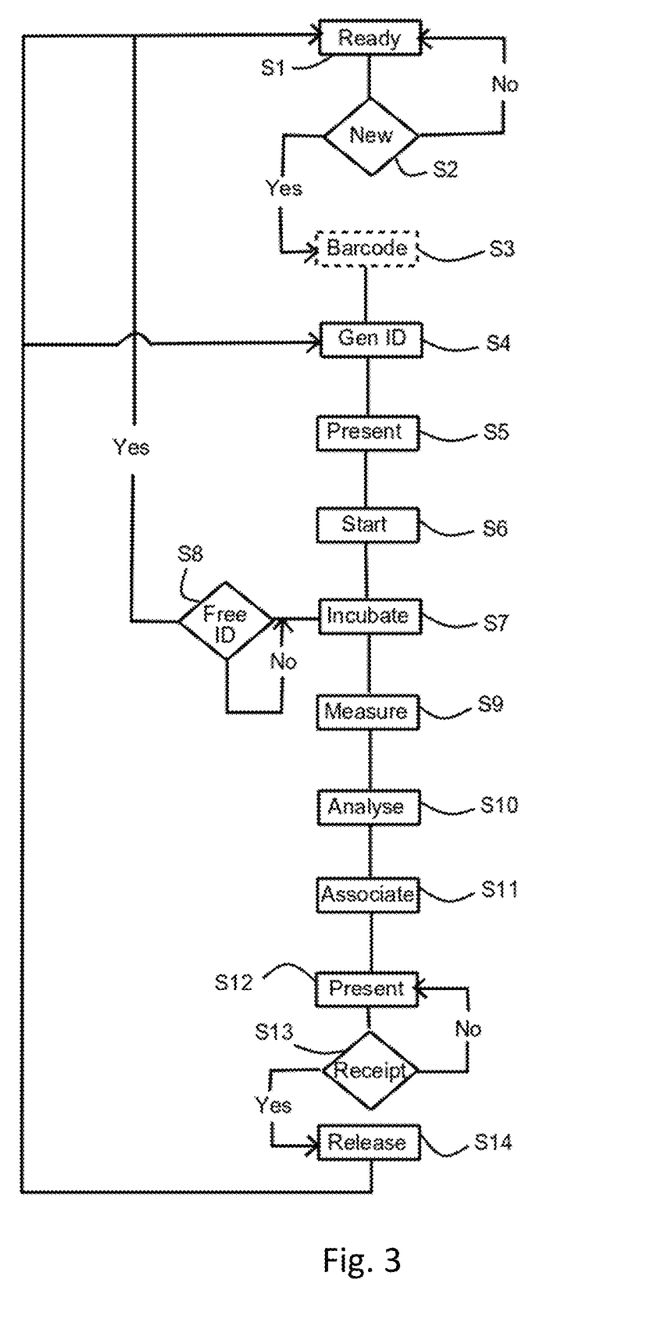
FIG. 3 is a flow chart showing the operation of an analysis instrument according to the present invention.

The operation of the analysis instrument according to the present invention will now be described with reference to the flow chart presented in FIG. 3 and made with reference to the use of the milk analysis instrument 22 at a dairy intake plant at which milk tanker drivers (who are here the users of the instrument) require their milk cargos to be analysed before they can be further processed. In order to more easily explain the present invention it will be assumed that the total number of drivers permitted to have samples in the milk analysis instrument 22 at any one time is three. The identification section 10 is constructed to hold three different symbols in a memory (for example memory storage unit 16) for use as user IDs (say a square, a triangle and a circle).

The control unit 12 controls the operation of the presentation section 8 to display to a tanker driver a visual indication on the screen 56 of the presentation section 8 that the milk analysis instrument 22 is ready to receive a new sample (S1). The tanker driver may generate information that a sample container 26 has been placed in the pipetting station 24, for example by manually inputting the information through pressing a highlighted portion of the screen 56 or, as described above, by locating the sample container 26 carrying a barcode in the pipetting station 24 (S2) or by manually entering information via a user input section (not shown). When the milk analysis instrument 22 has determined that a new sample is present (S2—YES) the control unit 12 operates the reader 54 to read in the barcode information (S3) and the identification section 10 to generate a new user ID for the tanker driver (S4). In the present example, the identification section 10 operates to see which of the three possible symbols (square, circle or triangle) are currently unused and selects an unused symbol (circle say) as the tanker driver's ID. The control unit 12 then operates the presentation section 8 to immediately present this new user ID to the tanker driver (S5) by display on the screen 56 for viewing by the tanker driver and/or transmission to the tanker driver's mobile phone (in this case the truck driver's mobile phone number must be recorded, for example through entry using a keypad representation at a touch sensitive portion of the screen 56 or on a separate user input section). The tanker driver's ID is also passed to the memory storage unit 16 for later association by the control unit 12 with relevant analysis results and with barcode information read (S3) from the barcode on the sample container 26.

The control unit 12 then operates to initiate the analysis process (S6) and a aliquot of the milk is extracted from the sample container 26 via the first and the second pipettes 28,30 and into a well 32a of the incubation unit 32. The identification section 10 is then interrogated to see whether any user ID symbol is currently unused and if any exists (S8—YES) a new visual indication is provided on the screen 56 that the milk analysis instrument 22 is ready to receive a new sample (S1).

At the end of the incubation period (S7) the control unit 12 operates the sample receiving section to collocate a sample in an occupied well 32b with the third pipette 36 and extract it for injection into the flow stream 40 of the flow cytometer 38 for measurement (S9). The results of the measurement are analysed (S10) in the control unit 12 to determine whether the milk sample contains one or more analytes of interest and the results of this analysis is added to the tanker driver's ID and to any information initially read from the sample container at S3 which is stored in the memory storage unit 16 (S11).

At least the tanker driver's ID and information related to the analysis results is presented for receipt by the tanker driver (S12), for example displayed on a display screen 56 remote from the analysis instrument 22, and possibly after approval by a third party to whom information related to the analysis results obtained at step S10 is made available. In some embodiments at the analysis step S10 a determination is made, such as by a suitably programmed microprocessor which may be a part of the control unit 12, whether a measured level of analyte exceeds a preset threshold value. Information based on this comparison forms the information related to the analysis results and is displayed at step S12 for the tanker driver to see. This information may be directions to unload the tanker driver's cargo if the analyte level is at or below the preset threshold value or directions to obtain further analysis if the analyte level is above the preset threshold value. Additionally, the results of the analysis at step S10 may include detailed information regarding the composition of the milk which may be transmitted together with information read from the sample container at step S3 via the remote receiver 60;62 to, for example, an information management system, perhaps accessible by third parties, for further action.

After presenting the information at step S12 a determination is made whether or not the tanker driver has actually received the information (S13). In some embodiments a user input device, such as may be provided by a touch sensitive portion of the display screen 56 on which the tanker driver's ID and information related to the analysis results is presented for receipt by the tanker driver at step S12, is provided by which the tanker driver is required to acknowledge receipt of the information. The information may be continued to be displayed until such time as such acknowledgement is received (S13—NO). In other embodiments the information may be continued to be displayed for a preset time only. Upon expiry of this preset time or upon acknowledgement (S13—YES) by the tanker driver and/or a third party also receiving the information (at step S10) the control unit 12 may be configured to release the tanker driver's ID for re-use (S14) and remove the information from display. In some embodiments, at this step S14, any information held by the milk analysis instrument 22, such as that retained in memory storage unit 16, which relates to the sample may be erased. In this way the risk of confusion with information from other samples may be reduced.

Figure 4:
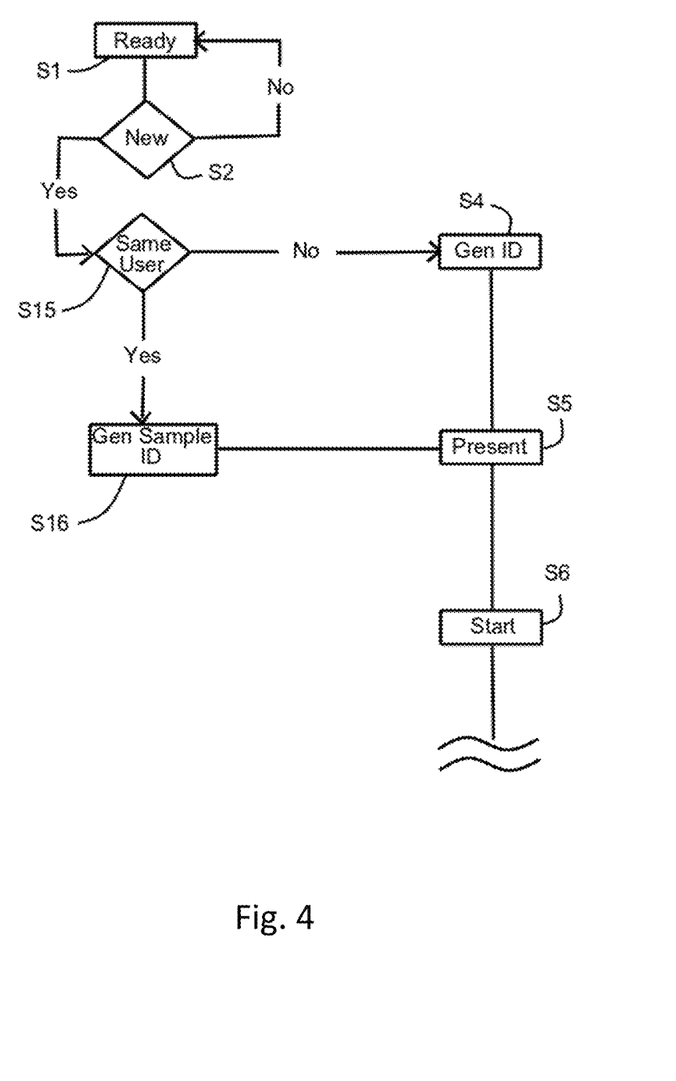
FIG. 4 is a flow chart showing operation of another embodiment of the analysis instrument according to the present invention.

Operation of another embodiment of the analysis instrument will now be described with reference to the flow chart presented in FIG. 4 whereby differences are illustrated in the operation between the present embodiment and the one previously described with reference to FIG. 3 for scenarios where a tanker driver presents more than one sample for analysis. This may occur for example, where samples are taken from different, physically isolated, compartments and it is necessary to know which sample results derive from which compartment.

Thus, in the present embodiment the operation of the milk analysis instrument 22 is modified in that after it is determined that a new sample (S2—YES) has been introduced the control unit 12 is configured to determine (S15) whether or not the new sample was introduced by a new user. To do this the user may for example, be prompted to press an appropriate portion of the display screen 56 or requested to provide appropriate input via a keyboard of a user input section (not shown) of the milk analysis instrument 22.

If the response (S15—NO) is such that it is determined in the control unit 12 that the user is a new user then the milk analysis instrument 22 operates to generate a new user ID (S4) and the operation of the instrument continues as previously discussed and the new user ID is presented to the tanker driver (S5).

If the response (S15—YES) is such that it is determined in the control unit 12 that the same user has presented a new sample then the instrument operates to generate a sample ID (S16) which is then presented (S5) to the tanker driver either alone or together with the driver's previously generated user ID.

The sample ID generated at step S16 may be, as with the user ID generated at step S4, a graphic symbol, an alphanumeric, a colour or a combination of these. For sake of example only, the sample ID is generated here as a number which increases sequentially for each new sample introduced by the same user. In certain embodiments the sample ID may be a colour and the pipetting station 24 may, in some of these embodiments, comprise a light source, such as an LED source, operable, for example under control of control unit 12, to generate and display light the same colour as the sample ID colour. The light source, in some embodiments, may be arranged to illuminate the sample container in the pipetting station 24 with its sample ID colour as a direct indicator to the user of the sample ID for that sample. It will be appreciated that samples from different users may have the same sample ID since the combination of user ID and sample ID will still be unique.

The sample ID is then stored for later association (S11) in the control unit 12 with analysis results and with the user ID and presented to the tanker driver (S12).

It will be appreciated that some or all of the operational steps described with reference to FIGS. 3 and 4 may be combined to provide other embodiments which fall within the scope of the invention as claimed whilst retaining the advantages described in respect of those steps. Moreover, the order of performance of the steps illustrated in these figures and described above is not necessarily the order referenced herein and some of the steps may be performed in parallel provided always that an identifier (user or user and sample) may be uniquely associated with the results of the analysis of a sample.

The invention claimed is:

1. An analysis instrument for performing analysis associated with one or more samples provided by each user of a plurality of users, the analysis instrument comprising:
   a sample receiving device configured to receive the one or more samples provided by each user of the plurality of users, the sample receiving device including a sample uptake device configured to extract an aliquot of each received sample of the one or more samples provided by each user of the plurality of users;
   an analysis device configured to receive the aliquot of each received sample from the sample receiving device, perform an analysis of each received aliquot, and generate an output based on the performed analysis, the output including information representative of results of the performed analysis;
   a display device configured to display information; and
   a controller communicatively coupled to each of the sample receiving device, the analysis device, and the display device, the controller configured to execute program code to
      for each separate user of the plurality of users, and in response to a determination that one or more particular samples are received at the sample receiving device from the separate user,
         generate an identifier that is unique to the separate user of the plurality of users and to the one or more particular samples, the identifier generated without user input from the separate user,
         control the sample receiving device to cause the sample uptake device to extract a particular aliquot of each particular sample of the one or more particular samples,
         control the analysis device to perform an analysis of each particular aliquot of each particular sample and to generate a particular output based on the performed analysis of each particular aliquot of each particular sample, such that the particular output corresponds to the one or more particular samples received from the separate user,
         associate at least a portion of the particular output with the identifier that is unique to the separate user, and
         supply the identifier and the portion of the particular output that is associated with the identifier to the display device and control the display device to display the identifier together with the portion of the particular output that is associated with the identifier,
      wherein the identifier consists of one or more of
         (i) one or more graphic symbols,
         (ii) one or more colours, or
         (iii) one or more numbers.

2. The analysis instrument according to claim 1, wherein the controller is further configured to execute the program code to generate one or more identifiers consisting of letters of an alphabet as the one or more graphic symbols.

3. The analysis instrument according to claim 1, wherein the controller is further configured to execute the program code to cause the display device to display the identifier separate from, and prior to,
   controlling at least the analysis device to perform the analysis of each particular aliquot of each particular sample and to generate the particular output based on the performed analysis of each particular aliquot of each particular sample, and displaying the identifier together with the portion of the particular output that is associated with the identifier.

4. The analysis instrument according to claim 1, wherein the display device includes a receiver communicatively coupled to the analysis device via a telecommunication device, the display device configured to receive the output from the analysis device via the telecommunication device.

5. The analysis instrument according to claim 1, wherein the controller is further configured to execute the program code to, for each separate user of the plurality of users, and in response to each determination that a separate particular sample of a plurality of particular samples is received at the sample receiving device from the separate user, generate a sample identifier that is unique to the separate particular sample of the plurality of particular samples as a part of the identifier that is unique to the separate user.

6. The analysis instrument according to claim 5, wherein
the analysis instrument includes a light source configured to emit light to illuminate at least a portion of the sample receiving device with light having one or more colours, and the controller is further configured to execute the program code to, in response to the determination that the separate particular sample of the plurality of particular samples is received at the sample receiving device from the separate user, generate a colour as the sample identifier that is unique to the separate particular sample, and control the light source to illuminate at least a portion of the sample receiving device at which the separate particular sample is received with light having the generated colour.

7. The analysis instrument according to claim 1, wherein
the controller includes a memory that stores a plurality of different unused identifiers, the plurality of different unused identifiers initially being not associated with any user of the plurality of users, and the controller is configured to execute the program code to, for each separate user of the plurality of users, and in response to the determination that the one or more particular samples are received at the sample receiving device from the separate user, generate the identifier that is unique to the separate user, without user input from the separate user, based on selecting one unused identifier of the plurality of different unused identifiers stored in the memory as one identifier that is unique to the separate user and the one or more particular samples that are received at the sample receiving device from the separate user.

8. A method of operating an analysis instrument, the method comprising:

receiving, at a sample receiving device, one or more particular samples from a separate user of a plurality of users; and in response to a determination that the one or more particular samples are received at the sample receiving device from the separate user, controlling the sample receiving device to extract an aliquot of each particular sample of the one or more particular samples, controlling an analysis device to perform an analysis of each aliquot of each particular sample received at the sample receiving device and to generate a particular output based on the performed analysis of each aliquot of each particular sample, such that the particular output corresponds to the one or more particular samples received from the separate user, generating an identifier that is unique to the separate user of the plurality of users and to the one or more particular samples, the identifier generated without user input from the separate user, the identifier consisting of one or more of (i) one or more graphic symbols, (ii) one or more colours, or (iii) one or more numbers, associating at least a portion of the particular output with the identifier that is unique to the separate user, and supplying the identifier and the portion of the particular output that is associated with the identifier to a display device and controlling the display device to display the identifier together with the portion of the particular output that is associated with the identifier.

9. The method according to claim 8, wherein the identifier consists of one or more letters of an alphabet as the one or more graphic symbols.

10. The method according to claim 8, further comprising:
causing the display device to display the identifier separate from, and prior to, controlling at least the analysis device to perform the analysis of each aliquot of each particular sample and to generate the particular output based on the performed analysis of each aliquot of each particular sample, and displaying the identifier together with the portion of the particular output that is associated with the identifier.

11. The method according to claim 8, wherein the display device receives the particular output at a receiver of the display device, from the analysis device via a telecommunication device.

12. The method according to claim 8, wherein the generating the identifier that is unique to the separate user of the plurality of users and to the one or more particular samples includes generating a sample identifier that is unique to a separate particular sample of a plurality of particular samples that is received at the sample receiving device from the separate user as a part of the identifier that is unique to the separate user.

13. The method according to claim 12, wherein the generating the identifier that is unique to the separate user of the plurality of users and to the one or more particular samples includes generating a colour as the sample identifier that is unique to the separate particular sample, and controlling a light source to illuminate at least a portion of the sample receiving device at which the separate particular sample is received with light having the generated colour.

14. The method according to claim 13, wherein the controlling the light source causes the light source to illuminate a sample container that is associated with the separate particular sample provided by the separate user and is located in the portion of the sample receiving device with the light having the generated colour.

15. The method according to claim 8, wherein
the generating the identifier that is unique to the separate user of the plurality of users and to the one or more particular samples includes selecting one unused identifier, of a plurality of different unused identifiers stored in a memory and initially being not associated with any user of the plurality of users, as one identifier that is unique to the separate user and the one or more particular samples that are received at the sample receiving device from the separate user.

16. The analysis instrument according to claim 6, wherein the controlling the light source causes the light source to illuminate a sample container that is associated with the separate particular sample provided by the separate user and is located in the portion of the sample receiving device with the light having the generated colour.

17. A non-transitory computer-readable medium storing a program of instructions that are executable to cause a microprocessor to perform a method to operate an analysis instrument, the method comprising:
    receiving, at a sample receiving device, one or more particular samples from a separate user of a plurality of users; and
    in response to a determination that the one or more particular samples are received at the sample receiving device from the separate user,
        controlling the sample receiving device to extract an aliquot of each particular sample of the one or more particular samples,
        controlling an analysis device to perform an analysis of each aliquot of each particular sample received at the sample receiving device and to generate a particular output based on the performed analysis of each aliquot of each particular sample, such that the particular output corresponds to the one or more particular samples received from the separate user,
    generating an identifier that is unique to the separate user of the plurality of users and to the one or more particular samples, the identifier generated without user input from the separate user, the identifier consisting of one or more of
        (i) one or more graphic symbols,
        (ii) one or more colours, or
        (iii) one or more numbers; and
    associating at least a portion of the particular output with the identifier that is unique to the separate user, and
    supplying the identifier and the portion of the particular output that is associated with the identifier to a display device and controlling the display device to display the identifier together with the portion of the particular output that is associated with the identifier.

18. The non-transitory computer-readable medium according to claim 17, wherein the generating the identifier that is unique to the separate user of the plurality of users and to the one or more particular samples includes generating a sample identifier that is unique to a separate particular sample of a plurality of particular samples that is received at the sample receiving device from the separate user as a part of the identifier that is unique to the separate user.

19. The non-transitory computer-readable medium according to claim 18, wherein the generating the identifier that is unique to the separate user of the plurality of users and to the one or more particular samples includes
    generating a colour as the sample identifier that is unique to the separate particular sample, and
    controlling a light source to illuminate at least a portion of the sample receiving device at which the separate particular sample is received with light having the generated colour.

20. The non-transitory computer-readable medium according to claim 19, wherein the controlling the light source causes the light source to illuminate a sample container that is associated with the separate particular sample provided by the separate user and is located in the portion of the sample receiving device with the light having the generated colour.

\* \* \* \* \*